(12) United States Patent
Koshikawa et al.

(10) Patent No.: US 8,419,633 B2
(45) Date of Patent: Apr. 16, 2013

(54) LIGHT SOURCE APPARATUS AND ENDOSCOPE SYSTEM

(75) Inventors: Yutaka Koshikawa, Hachioji (JP); Ryo Machida, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 31 days.

(21) Appl. No.: 13/246,214

(22) Filed: Sep. 27, 2011

(65) Prior Publication Data

US 2012/0130175 A1    May 24, 2012

Related U.S. Application Data

(63) Continuation of application No. PCT/JP2011/056537, filed on Mar. 18, 2011.

(30) Foreign Application Priority Data

Apr. 1, 2010  (JP) ................................. 2010-085415

(51) Int. Cl.
    *A61B 1/06*    (2006.01)
(52) U.S. Cl.
    USPC ............................ 600/181; 600/178; 362/574
(58) Field of Classification Search .................. 600/178, 600/181; 359/889; 362/572, 574, 575, 282
    See application file for complete search history.

(56) References Cited

U.S. PATENT DOCUMENTS

| | | | | |
|---|---|---|---|---|
| 4,951,133 A | * | 8/1990 | Onoda | 348/68 |
| 4,983,019 A | * | 1/1991 | Ikuno et al. | 600/181 |
| 6,960,165 B2 | | 11/2005 | Ueno et al. | |
| 7,226,412 B2 | * | 6/2007 | Ueno et al. | 600/178 |
| 7,586,703 B2 | * | 9/2009 | Thollot et al. | 359/889 |
| 7,892,169 B2 | * | 2/2011 | Gono et al. | 600/178 |
| 8,303,493 B2 | * | 11/2012 | Yabe et al. | 600/178 |
| 2003/0139650 A1 | * | 7/2003 | Homma | 600/181 |
| 2005/0078175 A1 | | 4/2005 | Kaneko | |
| 2005/0096505 A1 | | 5/2005 | Imaizumi et al. | |
| 2008/0249368 A1 | * | 10/2008 | Takei | 600/178 |
| 2009/0059592 A1 | * | 3/2009 | Toriyama et al. | 362/282 |

FOREIGN PATENT DOCUMENTS

| | | |
|---|---|---|
| EP | 1 527 729 A1 | 5/2005 |
| JP | 2005-131130 | 5/2005 |
| JP | 2006-271871 | 10/2006 |
| JP | 2007-029453 | 2/2007 |

OTHER PUBLICATIONS

European Search Report dated Feb. 7, 2012 from corresponding European Patent Application No. EP 11 76 5359.2.

\* cited by examiner

*Primary Examiner* — John P Leubecker
(74) *Attorney, Agent, or Firm* — Scully, Scott, Murphy & Presser, P.C.

(57) ABSTRACT

A light source apparatus includes a first rotational filter section that can place a blue filter, a green filter and a magenta filter in a light path, a second rotational filter section that can place a yellow filter in the light path and a band selection filter section that can place an NBI filter that limits blue and green light to a narrow band, wherein the first and the second rotational filter sections are controllable so that in the case of normal light imaging, the yellow filter is placed in the light path when the magenta filter is placed in the light path and in the case of narrow band imaging, the NBI filter is placed in the light path LP and the yellow filter is placed in the light path when the green filter is placed in the light path.

12 Claims, 12 Drawing Sheets

LIGHT SOURCE APPARATUS AND ENDOSCOPE SYSTEM

CROSS REFERENCE TO RELATED APPLICATION

This application is a continuation application of PCT/JP2011/056537 filed on Mar. 18, 2011 and claims benefit of Japanese Application No. 2010-085415 filed in Japan on Apr. 1, 2010, the entire contents of which are incorporated herein by this reference.

BACKGROUND OF THE INVENTION

1. Field of the Invention

The present invention relates to a light source apparatus which supplies illuminating light to a medical endoscope inserted into a subject for observing a tissue in a body and an endoscope system having the light source apparatus, and more particularly, to a light source apparatus that supplies illuminating light for white light imaging and special light imaging, and an endoscope system having the light source apparatus.

2. Description of the Related Art

Since sites to be observed are located inside a living body, medical endoscopes require a light source apparatus for illuminating the interior of the body. Illuminating light generated by the light source apparatus illuminates a target tissue from a distal end portion where an image pickup section is located via a light guide which is inserted into an insertion portion of the endoscope.

As for imaging using an endoscope, normal light imaging using visible light (white light imaging: WLI) is generally performed and various kinds of special light imaging utilizing wavelength characteristics of irradiating light are also performed.

For example, Japanese Patent Application Laid-Open Publication No. 2007-29453 discloses a frame-sequential endoscope system to perform narrow band imaging, auto fluorescence imaging and infrared imaging or the like as special light imaging.

In narrow band imaging (NBI), in order to observe blood vessels with high contrast, with attention focused on the utilization of light that has features of being strongly absorbed by blood as well as being strongly reflected/scattered by the mucosal epithelium, blue narrow band light and green narrow band light are sequentially radiated to thereby highlight the contrast between the capillary vessel of the mucosal epithelium and a deep thick blood vessel.

In auto fluorescence imaging (AFI), excitation light for observing fluorescence from a fluorescent substance such as collagen and light of a wavelength absorbed by hemoglobin in the blood are sequentially radiated to highlight a tumorous lesion and a normal mucous membrane with different color tones.

In infrared imaging (IRI), indocyanine green (ICG) through which infrared light is easily absorbed is intravenously injected and two infrared light beams having different wavelengths are sequentially radiated to thereby highlight a blood vessel of the deep mucous membrane which is not easily recognizable to human eyes and blood flow information.

Japanese Patent Application Laid-Open Publication No. 2007-29453 discloses the use of irradiating light passing through a normal red, green or blue primary color filter and a filter that passes light of a relatively wide wavelength band to prevent damage to an endoscope by heat of infrared light.

SUMMARY OF THE INVENTION

A light source apparatus of an embodiment that can supply illuminating light for normal light imaging and special light imaging includes a light source section that generates wideband light, a first rotational filter section that can place a first filter that passes light of a first wavelength band, a second filter that passes light of a second wavelength band having a longer wavelength than the first wavelength band or a third filter that passes light of a third wavelength band having a longer wavelength than the second wavelength band and light of the first wavelength band in a light path of the wideband light generated by the light source section, a second rotational filter section that can place a fourth filter that passes light of the second wavelength band and light of the third wavelength band in the light path, and a band selection filter section that can place a band limiting filter that limits light of the first wavelength band and light of the second wavelength band to a narrow band and intercepts light of the third wavelength band in the light path, wherein in a case of the normal light imaging, the first rotational filter section and the second rotational filter section are controllable so that the fourth filter is placed in the light path when the third filter is placed in the light path and in a case of the special light imaging, the band limiting filter is placed in the light path and the first rotational filter section and the second rotational filter section are controllable so that the fourth filter is placed in the light path when the second filter is placed in the light path.

Furthermore, an endoscope system according to another embodiment that can perform normal light imaging and special light imaging includes an insertion portion that includes an image pickup section at a distal end portion and a light guide inserted therein, a light source apparatus that supplies illuminating light via the light guide, an image processing unit that processes an image picked up by the image pickup section and a control section, wherein the light source apparatus includes a first rotational filter section that can place a first filter that passes light of a first wavelength band, a second filter that passes light of a second wavelength band having a longer wavelength than the first wavelength band or a third filter that passes light of a third wavelength band having a longer wavelength than the second wavelength band and light of the first wavelength band in a light path of the wideband light generated by the light source section, a second rotational filter section that can place a fourth filter that passes light of the second wavelength band and light of the third wavelength band in the light path, and a band selection filter section that can place a band limiting filter that limits light of the first wavelength band and light of the second wavelength band to a narrow band and intercepts light of the third wavelength band in the light path and the control section controls, in a case of the normal light imaging, the first rotational filter section and the second rotational filter section so that the fourth filter is placed in the light path when the third filter is placed in the light path, places, in a case of the special light imaging, the band limiting filter in the light path and controls the first rotational filter section and the second rotational filter section so that the fourth filter is placed in the light path when the second filter is placed in the light path.

DETAILED DESCRIPTION OF THE PREFERRED EMBODIMENTS

<First Embodiment>

Figure 1:
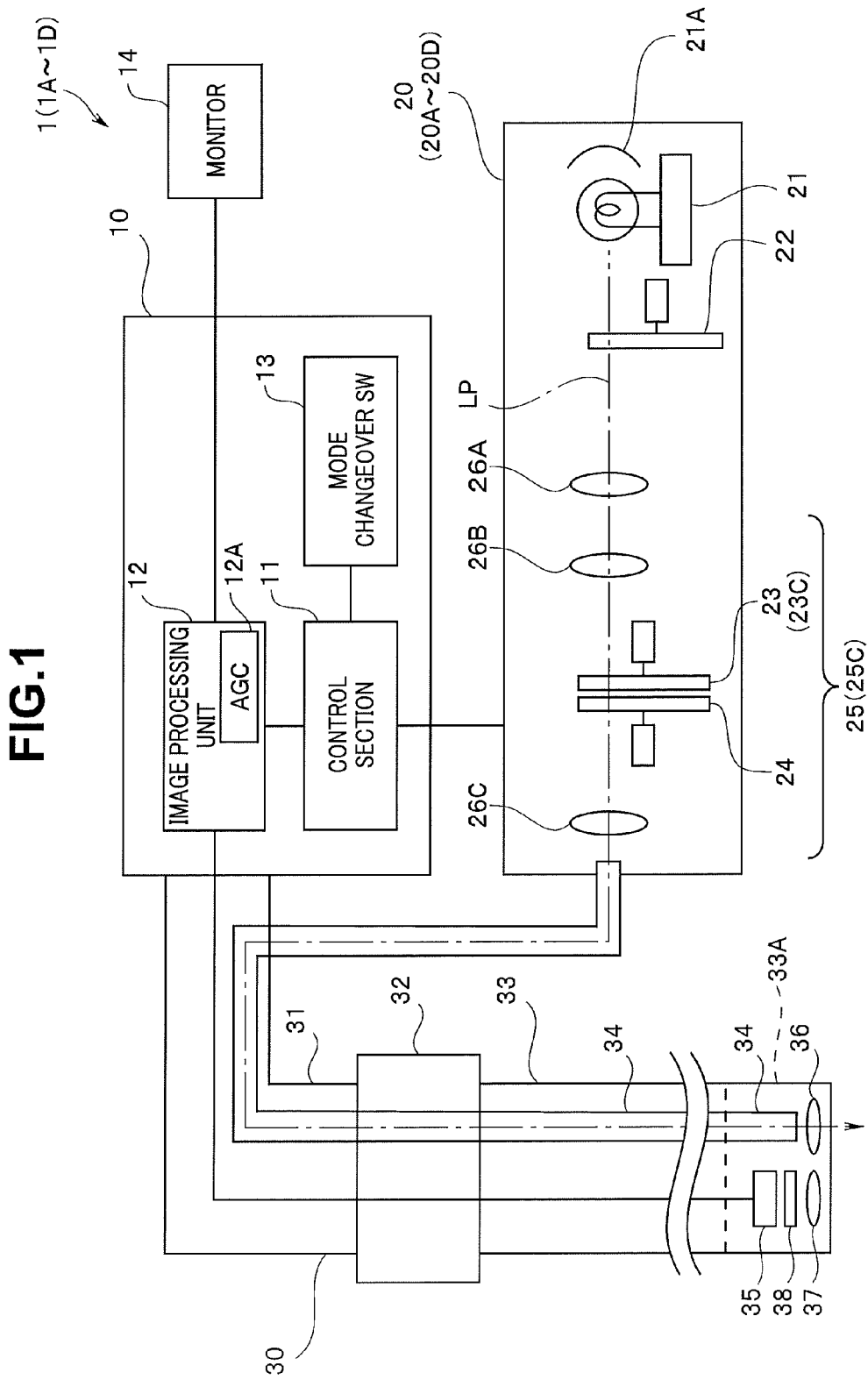
FIG. 1 is a configuration diagram of an endoscope system according to a first embodiment.

An endoscope system 1 according to a first embodiment of the present invention can perform narrow band imaging as special light imaging in addition to normal light imaging. That is, as shown in FIG. 1, the endoscope system 1 has a light source apparatus 20 that can alternatively supply illuminating light for normal light imaging and narrow band imaging, a main unit 10 and an endoscope 30. The endoscope 30 includes an operation section 32, an elongated insertion portion 33 inserted into the digestive tract or the like of a subject and a universal cable 31. A distal end portion 33A of the insertion portion 33 is provided with an image pickup optical section 37, a CCD 35 which is a frame-sequential image pickup section and an illuminating optical section 36 that emits illuminating light. The illuminating light from the light source apparatus 20 is guided to the illuminating optical section 36 through a light guide 34 that passes through the insertion portion 33. A cut filter 38 is placed in a light path of the image pickup optical section 37 to cut unnecessary reflected light as required.

The light source apparatus 20 includes a xenon lamp 21 which is a light source section, a band selection filter section 22, a rotational filter unit 25 made up of a first rotational filter section 23 and a second rotational filter section 24 and optical sections 26A, 26B and 26C, and supplies wideband light generated by the xenon lamp 21 to the light guide 34 as illuminating light according to an observation mode. The optical sections 26A, 26B and 26C are lenses to control luminous flux of illuminating light. The light source section is not limited to the xenon lamp 21 as long as it is a light source that generates wideband light ranging from visible light to infrared light. Furthermore, the xenon lamp 21 is provided with a minor 21A which also reflects light generated in a rear direction forward.

The main unit 10 has an image processing unit 12, a changeover switch 13 for the operator to select an observation mode and a control section 11 that controls the endoscope system 1 as a whole, and has a monitor 14 connected thereto. The image processing unit 12 having a signal amplification circuit (AGC) 12A synthesizes a plurality of images of a subject by illuminating light via different color filters after brightness adjustment and outputs a color image or pseudo-color image. The changeover switch 13 may also be provided in the operation section 32.

Figure 2A:
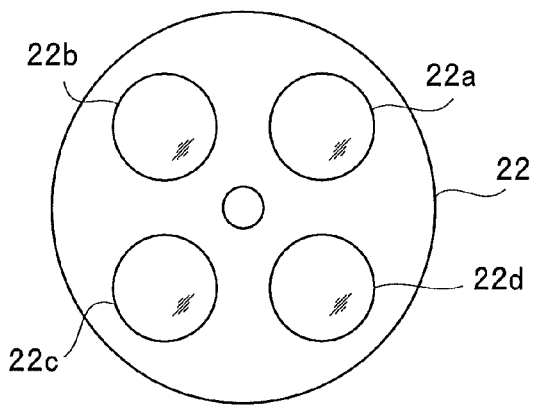
FIG. 2A is a plan view illustrating a structure of a filter.

As shown in a front view in FIG. 2A, the band selection filter section 22 is a turret that has a plurality of band limiting filters (band-pass filters) 22a to 22d in openings of a metal disk and can place a band limiting filter for a selected observation mode in a light path LP by rotating around the axis of rotation. For example, the band limiting filter 22a is a UV-IR cut filter, the band limiting filter 22b is a composite filter made up of two filters; an NBI filter and a UV-IR cut filter, the band limiting filter 22c is a composite filter made up of two filters; an AFI filter and a UV-IR cut filter and the band limiting filter 22d is an IRI filter. Although characteristics of the above-described filters will be described later, the light source apparatus 20 may be provided with at least the band limiting filters 22a and 22b.

Furthermore, some openings of the metal disk may be cavities without any filter placed therein or provided with transparent glass so as to pass whole light. The band selection filter section 22 may also be a band selection filter section that has two independently rotatable metal disks and combines respective metal disk filters to be used as a composite filter.

Figure 2B:
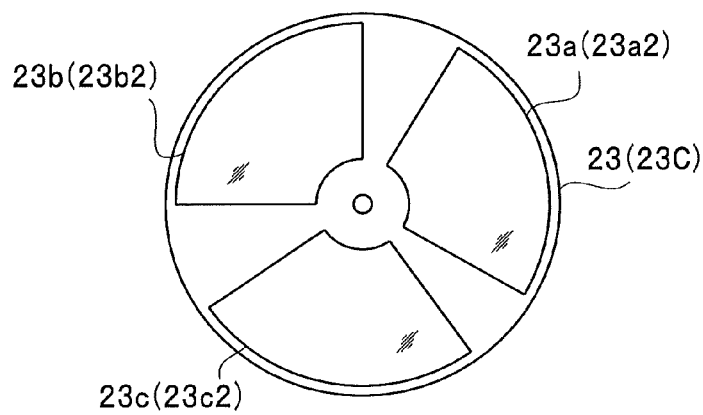
FIG. 2B is a plan view illustrating a structure of a filter.
Figure 2C:
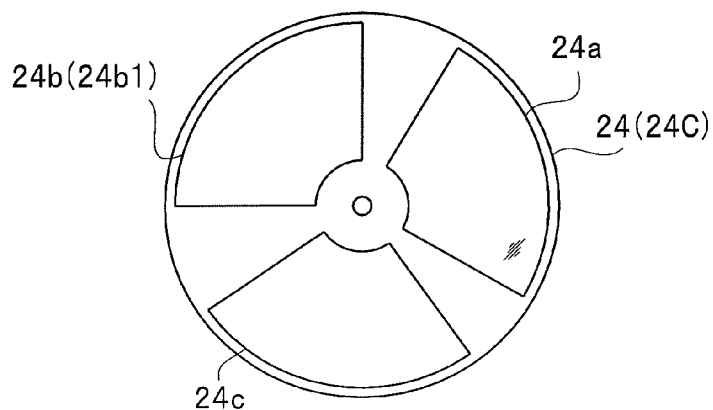
FIG. 2C is a plan view illustrating a structure of a filter.

As shown in a front view of FIG. 2B, the first rotational filter section 23 arranges a blue (B) filter 23a which is a first filter that passes light of a blue wavelength band, a green (G) filter 23b which is a second filter that passes light of a green wavelength band and a magenta (Mg) filter 23c which is a third filter that passes light of red and blue wavelength bands in three arc-shaped openings on the same circumference of a metal disk. On the other hand, as shown in FIG. 2C, the second rotational filter section 24 arranges a yellow (Ye) filter 24a which is a fourth filter that passes light of green and red wavelength bands in one of arc-shaped openings on the same circumference of a metal disk.

That is, of the color pass filters, the B filter 23a and the G filter 23b are primary color filters and the Mg filter 23c and the Ye filter 24a are complementary color filters.

The first rotational filter section 23 and the second rotational filter section 24 of the rotational filter unit 25 continuously rotate around the same axis of rotation and illuminating light beams of their respective colors are thereby sequentially radiated onto the subject. There may also be an opening that passes all visible light beams. The rotational filter unit 25 can control a filter placed in the light path LP by the first rotational filter section 23 and the second rotational filter section 24 simultaneously. In other words, the control section 11 controls the first rotational filter section 23 and the second rotational filter section 24 as described above.

For example, the control section 11 performs control such that relative positions in the rotation direction of the second rotational filter section 24 and the first rotational filter section 23 are set to predetermined positions and then fixes the second rotational filter section 24 and the first rotational filter section 23. For this reason, when the first rotational filter section 23 rotates, the second rotational filter section 24 fixed to the first rotational filter section 23 also rotates simultaneously. The first rotational filter section 23 and the second rotational filter section 24 may also be able to rotate independently of each other as long as these filter sections can be subjected to synchronous control, that is, matched phase rotation control.

Figure 3A:
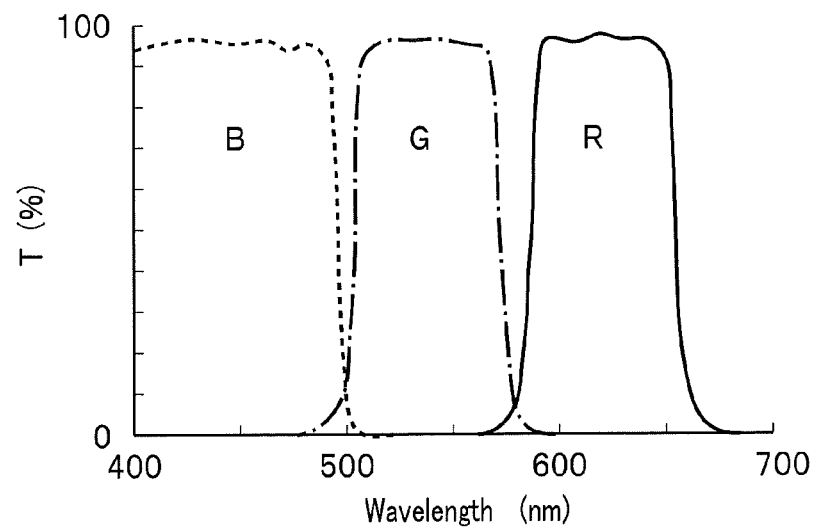
FIG. 3A is a graph illustrating transmission characteristics of filters.
Figure 3B:
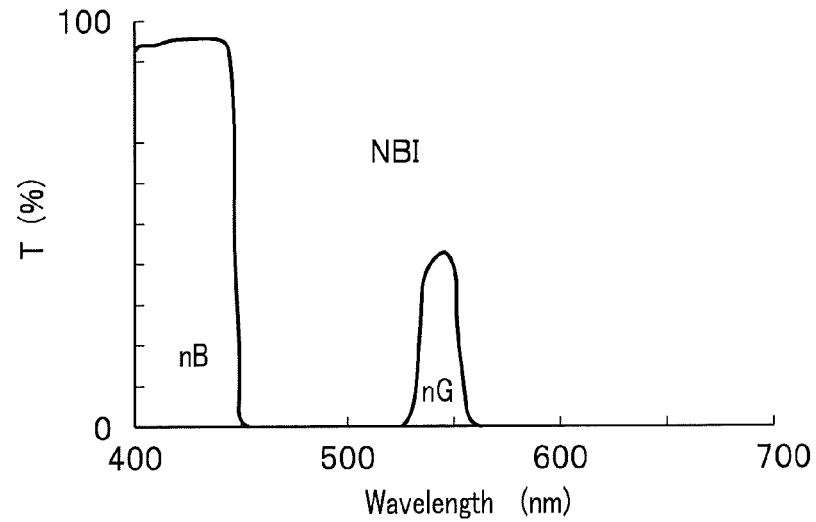
FIG. 3B is a graph illustrating transmission characteristics of filters.
Figure 3C:
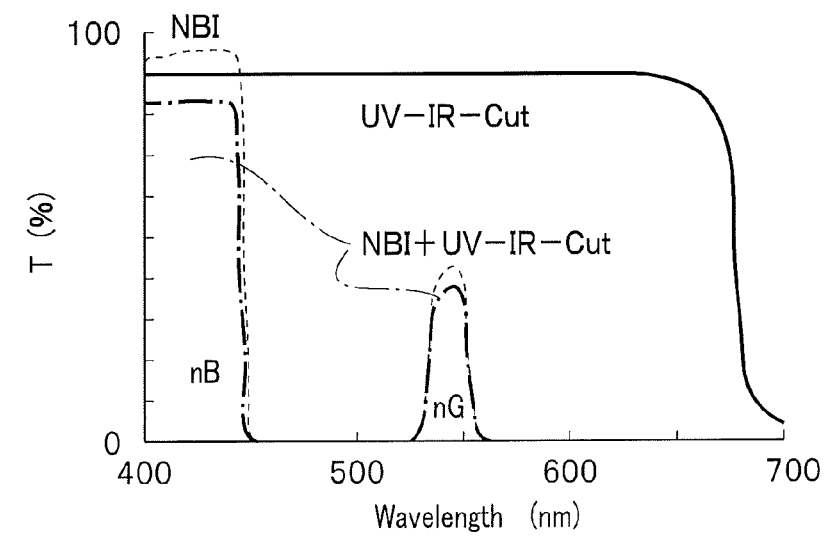
FIG. 3C is a graph illustrating transmission characteristics of filters.

Here, for a comparison, a publicly known frame-sequential endoscope system will be described. FIG. 3A to FIG. 3C are graphs illustrating transmission characteristics of the filters of the rotation unit, and the horizontal axis represents a wavelength and the vertical axis represents a transmittance. FIG. 3A shows transmission characteristics of three primary color filters that pass red (R), green (G) and blue (B) light beams respectively, FIG. 3B shows a transmission characteristic of an NBI filter that limits blue light (B) and green light (G) to discrete narrow band light beams (nB, nG) and also intercepts red light, and FIG. 3C shows a transmission characteristic of a UV-IR cut filter that intercepts light other than the visible light region and a transmission characteristic when the NBI filter and the UV-IR cut filter are combined.

As shown in FIG. 3A, the transmittance of the B filter 23a is 50% or above at 495 nm or below and 93% or above at 480 nm or below. The transmittance of the G filter 23b is 50% or above at 500 to 575 nm and 93% or above at 515 to 560 nm. The transmittance of the R filter is 50% or above at 585 to 655 nm and 93% or above at 600 to 640 nm. As shown in FIG. 3B, the transmittance of the NBI filter is 50% or above at 445 nm or below and less than 1% at 455 nm to 510 nm, but is higher again at 520 to 560 nm. As shown in FIG. 3C, the UV-IR cut filter passes light of the visible light region (400 to 675 nm). In the transmission characteristics of the filters, when an upper limit or lower limit of the wavelength band is not explicitly shown, the upper limit or lower limit may be at least an upper limit or lower limit of the visible light region.

Figure 4A:
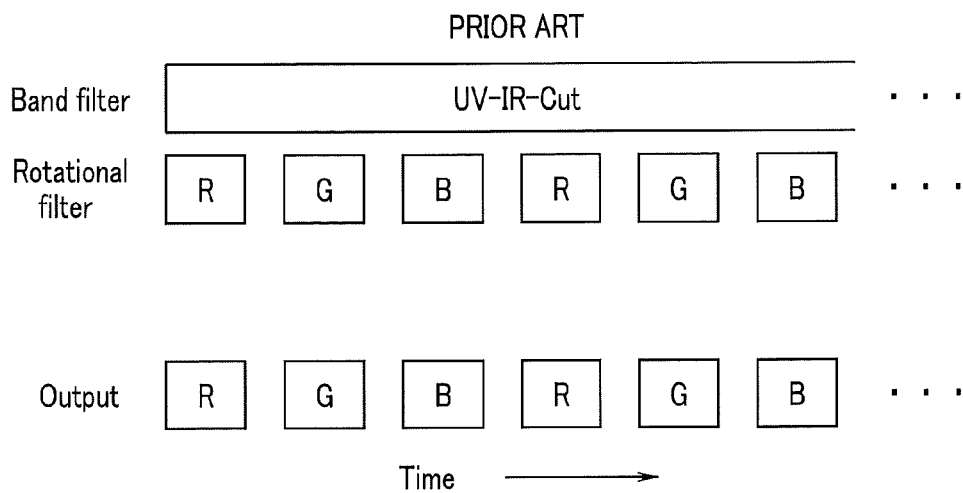
FIG. 4A is a diagram illustrating irradiating light in a publicly known endoscope system.
Figure 4B:
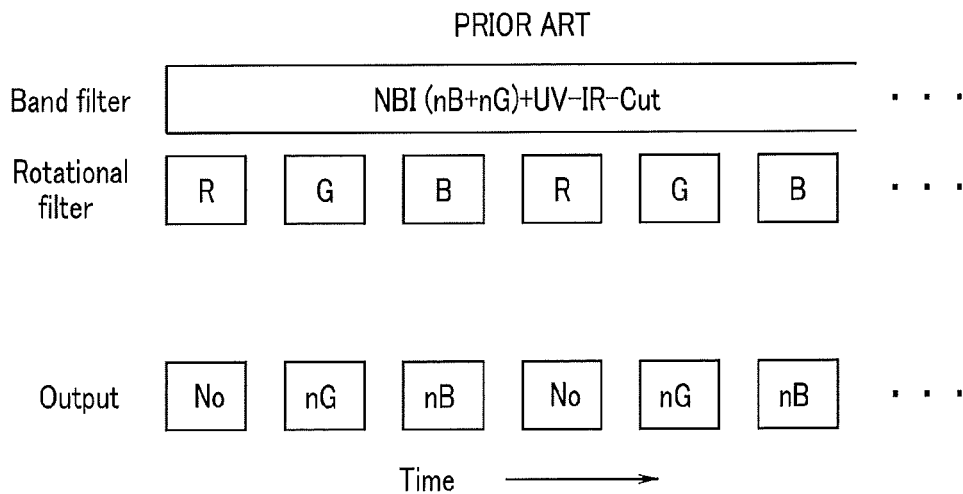
FIG. 4B is a diagram illustrating irradiating light in a publicly known endoscope system.

FIG. 4A and FIG. 4B are diagrams illustrating a relationship between a filter placed in the light path LP of the frame-sequential endoscope system and irradiating light, and the horizontal axis represents a tune. As shown in FIG. 4A, in normal light imaging (WLI), a UV-IR cut filter of the band selection filter section is always placed in the light path LP and light outside the visible light region is intercepted. When the rotational filter section continuously rotates, illuminating light is intermittently intercepted and red (R), green (G) and blue (B) beams are sequentially and continuously radiated onto the subject. Three images of the subject obtained per color (black and white image with only a brightness signal) are time-sequentially picked up by the CCD 35, synthesized in the image processing unit 12 and displayed on the monitor 14 as one color image.

That is, since one color image is synthesized assuming one rotation of the rotational filter as one cycle, the frame rate of a moving image is determined by the rotation speed of the rotational filter.

On the other hand, in narrow band imaging (NBI), the NBI filter and the UV-IR cut filter of the band selection filter section are always placed in the light path LP. For this reason, as shown in FIG. 4B, when the rotational filter section continuously rotates, narrow band blue light (nB) and narrow band green light (nG) are sequentially and continuously radiated onto the subject. Two images obtained by narrow band blue light (nB) and narrow band green light (nG) are synthesized and displayed on the monitor as a pseudo-color image.

That is, as shown in FIG. 4B, while the red filter is placed in the light path of the rotational filter section in the publicly known endoscope system, all light generated by the light source is cut (No), and therefore no image is obtained. Furthermore, since blue light is more likely to attenuate than green light while being guided through the light guide 34, an image of the subject illuminated with narrow band blue light (nB) is darker than an image of the subject illuminated with narrow band green light (nG). Although a signal can be amplified by the signal amplification circuit (AGC) 12A of the image processing unit 12, amplification causes noise to increase and image quality may thereby deteriorate.

Figure 5A:
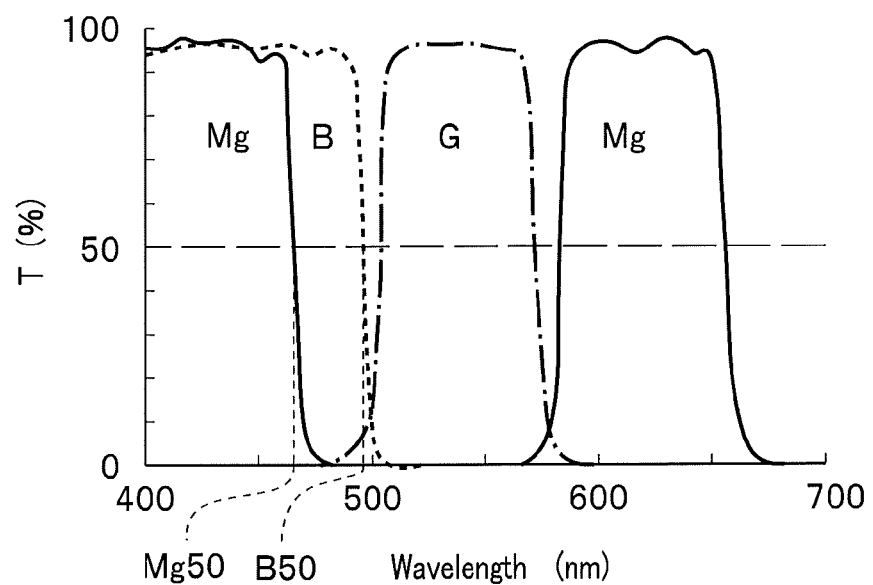
FIG. 5A is a graph illustrating transmission characteristics of filters.
Figure 5B:
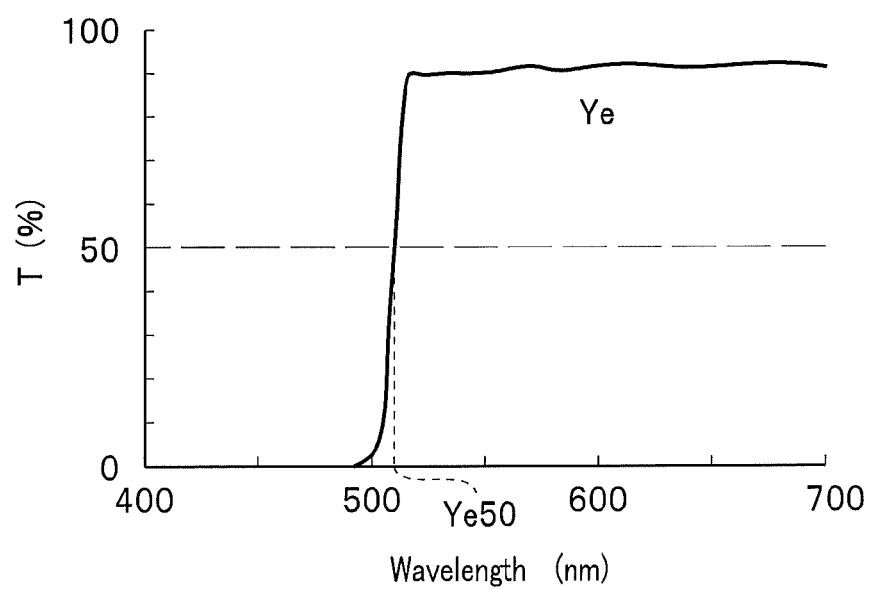
FIG. 5B is a graph illustrating a transmission characteristic of a filter.

By contrast, in the endoscope system 1 of the present embodiment, the first rotational filter section 23 of the rotational filter unit 25 is provided with the B filter 23a, the G filter 23b and the Mg filter 23c having the transmission characteristics shown in FIG. 5A and the second rotational filter section 24 is provided with the Ye filter 24a having the transmission characteristic shown in FIG. 5B.

Figure 6A:
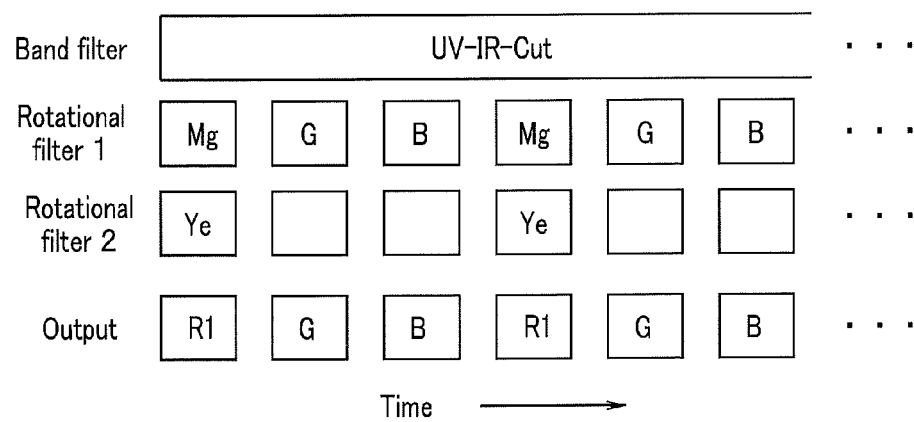
FIG. 6A is a diagram illustrating irradiating light in an endoscope system according to a first embodiment.

In normal light imaging (WLI), as shown in FIG. 6A, the control section 11 controls the first and second rotational filter sections 23 and 24 (rotational filter unit 25) such that the Ye filter 24a of the second rotational filter section 24 is placed in the light path LP when the Mg filter 23c of the first rotational filter section 23 is placed in the light path LP. That is, when normal light imaging is selected through operation of the mode changeover SW 13 by the operator, the control section 11 rotates the Ye filter 24a of the second rotational filter section 24 to a position where the Ye filter 24a overlaps with the Mg filter 23c of the first rotational filter section 23, and then fixes the second rotational filter section 24 and the first rotational filter section 23. The control section 11 then continuously rotates the first rotational filter section 23. In the light source apparatus 20, the openings 24b and 24c of the second rotational filter section 24 are cavities.

As shown in FIG. 6A, in normal light imaging (WLI), when the first rotational filter section 23 and the second rotational filter section 24 continuously rotate, illuminating light is intermittently intercepted and red R1, green (G) and blue (B) light beams are sequentially radiated onto the subject. Three images of the subject obtained per color by the image pickup section (black and white images with only a brightness signal) are time-sequentially picked up by the CCD 35, synthesized by the image processing unit 12 and displayed on the monitor 14 as one color image.

Here, red R1 is irradiating light that passes through the Mg filter 23c and the Ye filter 24a. That is, as shown in FIG. 5A, the irradiating light that passes through the Mg filter 23c includes light of a blue wavelength band and light of a red wavelength band, and becomes light of a red wavelength band (red R1) by further passing through the Ye filter 24a.

In narrow band imaging (NBI), the NBI filter (FIG. 3C) in the band selection filter section 22 is placed in the light path LP and the first and second rotational filter sections 23 and 24 are controlled such that the Ye filter 24a of the second rotational filter section 24 is placed in the light path LP when the G filter 23b of the first rotational filter section 23 is placed in the light path LP. That is, when narrow band imaging is selected through the operation of the mode changeover SW 13, the control section 11 rotates the second rotational filter section 24 to a position where the G filter 23b and the Ye filter 24a overlap with each other and fixes the second rotational filter section 24. The control section 11 then controls the first rotational filter section 23 so as to continuously rotate.

Figure 6B:
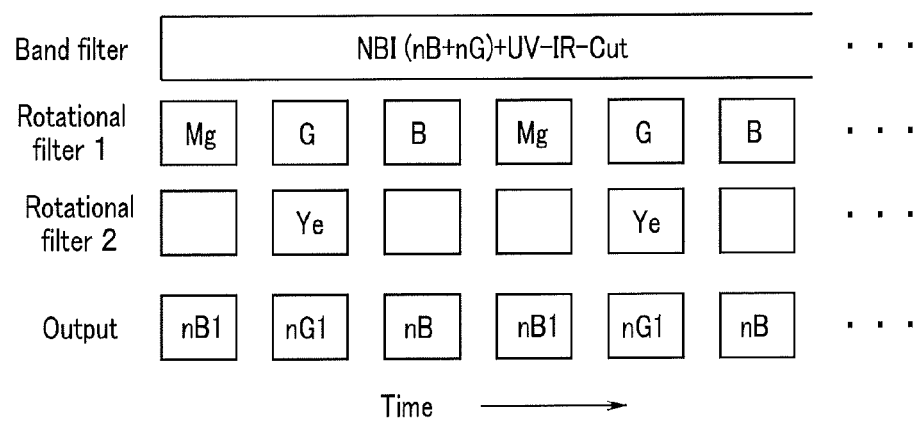
FIG. 6B is a diagram illustrating irradiating light in the endoscope system according to the first embodiment.

Thus, as shown in FIG. 6B, when the first rotational filter section 23 and the second rotational filter section 24 rotate, narrow band blue light (nB1), narrow band green light (nG1) and narrow band blue light (nB) are sequentially radiated onto the subject. Here, the narrow band blue light (nB1) is irradiating light that has passed through the NBI filter and the Mg filter 23c and the narrow band green light (nG1) is irradiating light that has passed through the NBI filter, the G filter 23b and the Ye filter 24a.

That is, in the endoscope system 1, even when the Mg filter 23c is placed in the light path of the first rotational filter section 23, narrow band blue light (nB1) is radiated onto the subject. For this reason, the image processing unit 12 applies addition processing to the image obtained by narrow band blue light (nB1) and the image obtained by narrow band blue light (nB), and can thereby obtain a brighter narrow band blue light image. That is, the endoscope system 1 can make brighter a narrow band blue light image which is darker in the conventional endoscope system than an image obtained by narrow band green light (nG1) by applying addition processing to the two images. For this reason, the endoscope system 1 can cause the monitor 14 to display a pseudo-color image of high image quality achieving a balance between narrow band green light (nG1) and narrow band blue light (nB+nB1).

As shown in FIG. 5A, in the endoscope system 1, the half width wavelength (Mg50) in the blue region of the Mg filter 23c is 465 nm and is located on the shorter wavelength side than the half width wavelength (B50) 495 nm on the longer wavelength side of the B filter 23a. Here, the half width wavelength refers to a wavelength where the transmittance becomes 50%. Furthermore, the difference between the half width wavelength (Mg50) of 465 nm in the blue region of the Mg filter 23c and the half width wavelength (Ye50) of 510 nm on the shorter wavelength side of the Ye filter 24a shown in FIG. 5B is 45 nm, which falls within a range of 30 to 70 nm.

By combining the filters that satisfy the above-described conditions, the light source apparatus 20 can supply light in a desired wavelength region.

As described above, the light source apparatus 20 can obtain a brighter image in narrow band imaging and the endoscope system 1 provided with the light source apparatus 20 can obtain a brighter image in narrow band imaging.

<Modification Example of First Embodiment>

Next, an endoscope system 1A and a light source apparatus 20A according to a modification example of the first embodiment will be described. Since the endoscope system 1A or the like of the present modification example is similar to the endoscope system 1 or the like of the first embodiment, the same components will be assigned the same reference numerals and descriptions thereof will be omitted.

Figure 7:
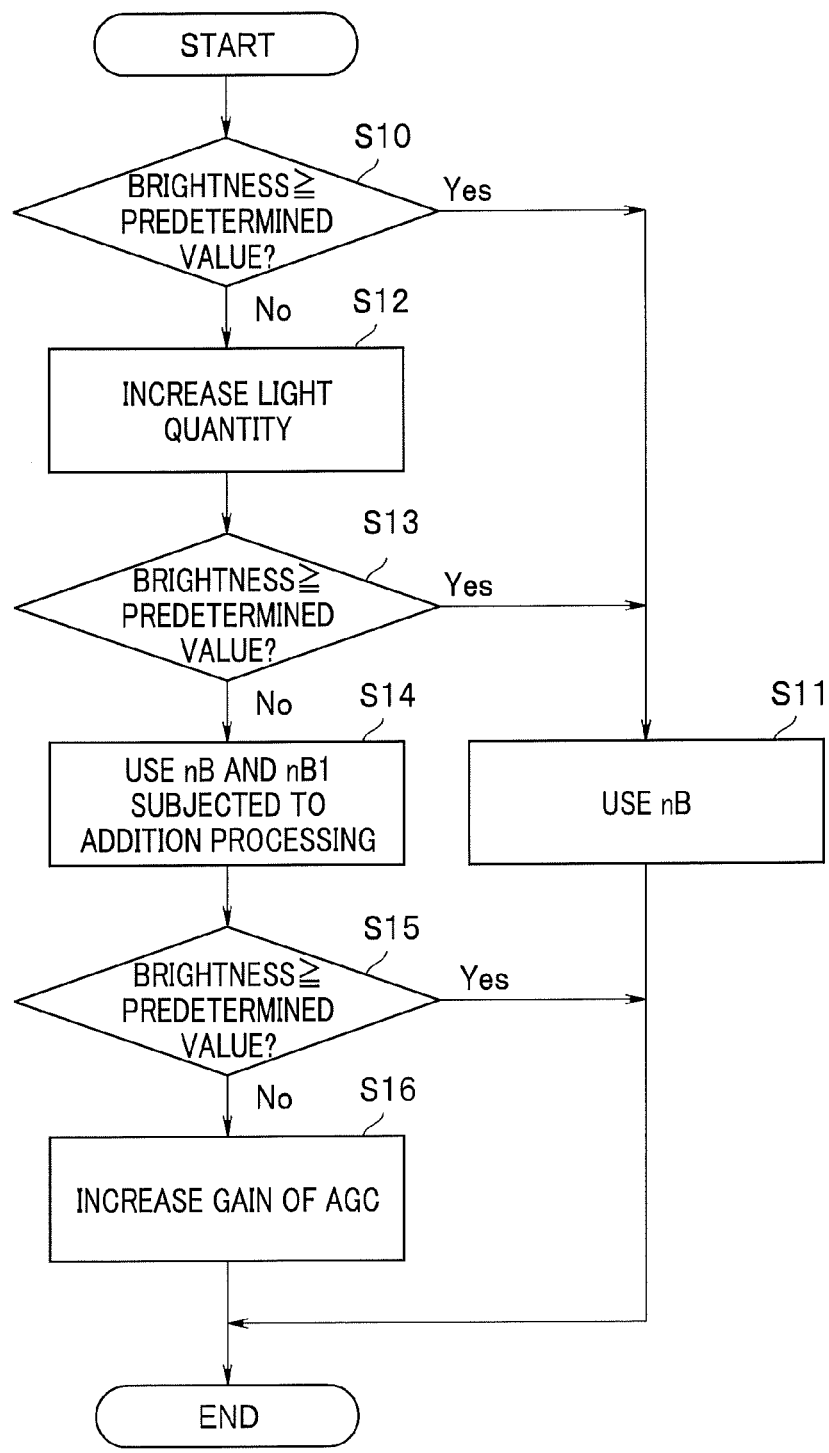
FIG. 7 is a flowchart illustrating a control method in an endoscope system according to a modification example of the first embodiment.

To make an image brighter, the current of the xenon lamp 21 of a light source apparatus 20A may be increased or a diaphragm (not shown) may be adjusted to increase the basic light quantity. Furthermore, a signal may be amplified more by increasing an amplification factor (gain) of an auto gain control (AGC) circuit 12A of the image processing unit 12. Thus, the endoscope system 1A performs control shown in a flowchart in FIG. 7.

<Step S10>

The image processing unit 12 decides whether brightness of an acquired image is a predetermined value or above.

<Step S11>

When the subject is located near the distal end portion 33A, brightness of the image is a predetermined value or above (S10: Yes), and therefore the image processing unit 12 synthesizes only an image obtained by narrow band blue light (nB) with an image obtained by narrow band green light (nG1) and creates a pseudo-color image. That is, the image obtained by narrow band blue light (nB1) is discarded. This is because, to be exact, the image obtained by narrow band blue light (nB) is different from the image obtained by narrow band blue light (nB1) in the image pickup time, and therefore using the image obtained by narrow band blue light (nB1) for a synthesis may cause image quality to deteriorate. Of course, the image obtained by narrow band blue light (nB1) may be used and the image obtained by narrow band blue light (nB) may be discarded instead.

<Step S12>

When brightness of an image is less than a predetermined value (S10: No), the control section 11 increases the current of the xenon lamp 21 or adjusts the diaphragm (not shown) to increase the basic light quantity of the light source apparatus 20. When the basic light quantity of the light source apparatus 20 is increased, image quality never deteriorates.

<Step S13>

The image processing unit 12 decides whether the brightness of the acquired image is a predetermined value or above. When the brightness of the image is a predetermined value or above (S13: Yes), in S11, the image processing unit 12 synthesizes only the image obtained by narrow band blue light (nB) with the image obtained by narrow band green light (nG1) to create a pseudo-color image.

<Step S14>

Even after setting the basic light quantity to a maximum level, if the brightness of the image is less than the predetermined value (S13: No), the image processing unit 12 applies addition processing to the image obtained by narrow band blue light (nB) and the image obtained by narrow band blue light (nB1) and increases the brightness of the image. Assuming an addition ratio α between the image obtained by narrow band blue light (nB) and the image obtained by narrow band blue light (nB1) to be variable, the images may be summed up with a weight of nB:α×nB1. For example, when α=0, only the image obtained by narrow band blue light (nB) is used and when α=0.5, an image with nB+0.5×nB1 is obtained and when α=1, an image of nB+nB1 is obtained.

<Step S15>

The image processing unit 12 decides whether or not the brightness of the acquired image is a predetermined value or above.

<Step S16>

When the brightness of the image is less than the predetermined value even after applying addition processing to the image (S15: No), the image processing unit 12 more amplifies (increases the gain of) the signal of the image by narrow band blue light subjected to addition processing by the AGC circuit 12A although this causes deterioration of an S/N. The amplification factor of the signal amplification processing by AGC circuit 12A is adjustable by setting a processing coefficient, and when the amplification factor is small, the S/N is improved and image quality deterioration can be substantially ignored.

The endoscope system 1A in the present modification example that performs the above-described control has the effects of the endoscope system 1 of the first embodiment and can further obtain a bright narrow band light image even when the distance between the subject and the distal end portion 33A changes while suppressing deterioration of image quality to a minimum.

<Second Embodiment>

Next, an endoscope system 1B according to a second embodiment will be described. Since the endoscope system 1B of the present embodiment is similar to the endoscope system 1 of the first embodiment, the same components will be assigned the same reference numerals and the descriptions thereof will be omitted.

The endoscope system 1B of the present embodiment can perform auto fluorescence imaging (AFI) as special light imaging in addition to normal light imaging. As already described, auto fluorescence imaging synthesizes a fluorescent image with an image by green light which is strongly absorbed by hemoglobin and displays a pseudo-color image which highlights a tumorous lesion and a normal mucous membrane with different color tones on the monitor 14. This takes advantage of a feature that a tumor tissue irradiated with blue excitation light has reduced auto fluorescence (fluorescence emitted by a fluorescent substance such as collagen present in the mucous membrane) compared to a normal tissue. As a result of the combination of a green light image which is affected not by hypertrophy of the mucous membrane but only by a variation of hemoglobin and the fluorescent image, a normal tissue is displayed in light green, a tumor tissue is displayed in magenta and a deep blood vessel is displayed in dark green. Of course, a fluorescent agent may be dispensed beforehand to observe the fluorescence from the fluorescent agent selectively concentrated on the target tissue.

The intensity of the fluorescence (F) is much smaller than that of blue light which is the excitation light. For this reason, the image pickup optical section 37 for auto fluorescence imaging is provided with the excitation light cut filter 38 which passes fluorescence (F) having a longer wavelength than the blue light but intercepts the blue light.

The endoscope system 1B can radiate not only narrow band blue light (nB3) that has passed through the B filter 23a but also narrow band blue light (nB2) that has passed through the Mg filter 23c onto the subject as the excitation light of a blue wavelength band. That is, in the publicly known endoscope system, the R filter is placed in the light path of the rotational filter section and can radiate narrow band blue light (nB2) in a time zone during which light is not irradiated.

Figure 8A:
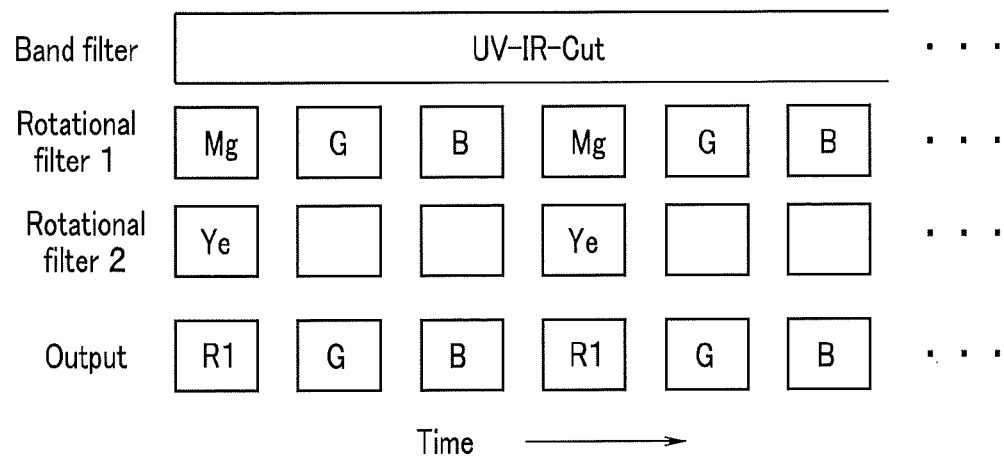
FIG. 8A is a diagram illustrating irradiating light in an endoscope system according to a second embodiment.
Figure 8B:
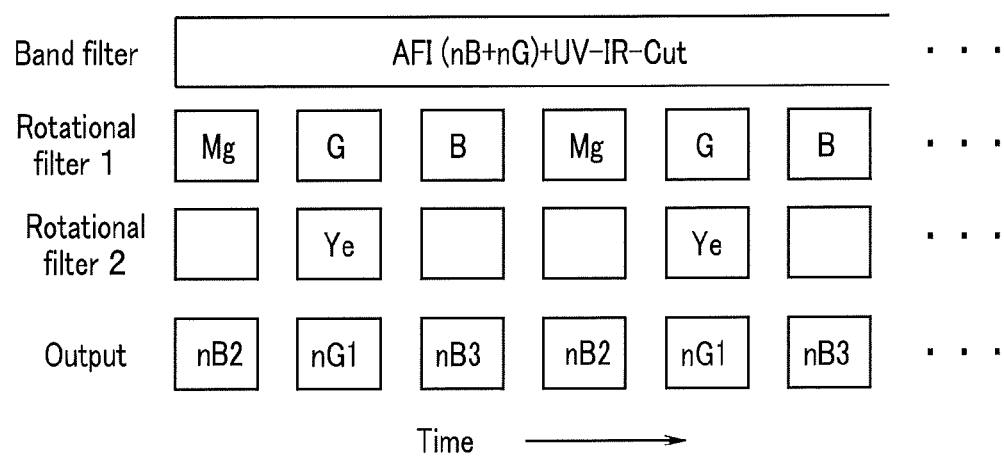
FIG. 8B is a diagram illustrating irradiating light in the endoscope system according to the second embodiment.

That is, as shown in FIG. 8A and FIG. 8B, the operation of the light source apparatus 20B is substantially the same as that of the light source apparatus 20, but a transmission wavelength band of the filter thereof is a little different. That is, as shown in FIG. 8B, in auto fluorescence imaging, the band selection filter section 22 is provided with the band limiting filter 22c (composite filter made up of two filters; AFI filter and UV-IR cut filter). The transmittance of the band limiting filter 22c is 85% or above at 400 to 430 nm and less than 1% at 460 to 480 nm, but 90% or above at 520 to 650 nm. The filters of the rotational filter unit 25 may be the same as or may be a little different from those of the endoscope system 1.

The light source apparatus 20B of the present embodiment can supply excitation light twice in one cycle in which the publicly known light source apparatus supplies excitation light once. Therefore, the light source apparatus 20B can cause a brighter image to be obtained in auto fluorescence imaging and the endoscope system 1 including the light source apparatus 20 can obtain a brighter image in auto fluorescence imaging.

<Third Embodiment>

Next, an endoscope system 1C and a light source apparatus 20C according to a third embodiment will be described. Since the endoscope system 1C of the present embodiment is similar to the endoscope system 1 or the like of the first embodiment, the same components will be assigned the same reference numerals and descriptions thereof will be omitted.

The endoscope system 1C of the present embodiment can perform narrow band imaging (NBI) and auto fluorescence imaging (AFI) as special light imaging in addition to normal light imaging (WLI). That is, the endoscope system 1C has the function of the endoscope system 1 as well as the function of the endoscope system 1B.

Figure 9:
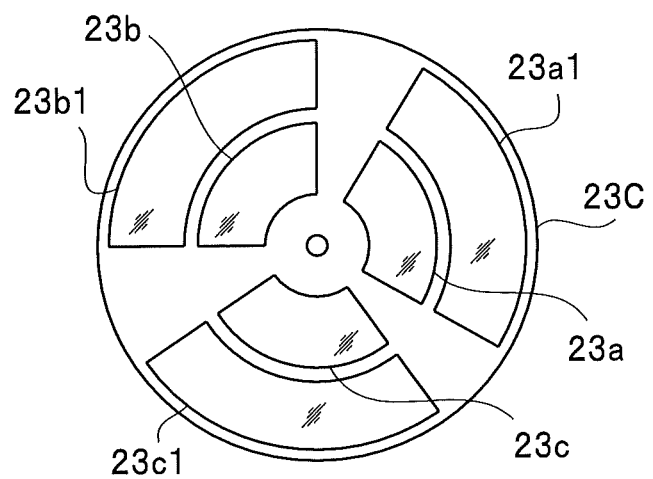
FIG. 9 is a plan view illustrating a structure of a rotational filter.

As shown in FIG. 9, the first rotational filter section 23C of the light source apparatus 20C has three filters including an Mg filter in an inner circumferential portion and three filters 23a1, 23b1 and 23c1 including a magenta 2 (Mg2) filter in an outer circumferential portion. The second rotational filter 24C has a Ye filter 24a for NBI and a yellow 2 (Ye2) filter 24b1 for AFI. The rotational filter unit 25C can move along a surface perpendicular to the light path LP and can place the inner circumferential portion or outer circumferential portion of the first rotational filter section 23C in the light path LP according to the observation mode. Furthermore, the band selection filter section 22 has three types of filter; for normal light imaging, for narrow band imaging and for auto fluorescence imaging and the filters corresponding to the respective observation modes are placed in the light path LP.

In normal light imaging, as already described, the Mg filter and the Ye filter or the Mg2 filter and the Ye2 filter are controlled so as to be simultaneously placed in the light path LP. The rotational filter unit 25C is then controlled so that the inner circumferential portion is placed in the light path LP in narrow band imaging, and the outer circumferential portion is placed in the light path LP in auto fluorescence imaging. Their respective operations or the like in special light imaging are the same as those of the already described endoscope systems 1 to 1B.

The endoscope system 1C has the effects of the endoscope system 1 and can further perform narrow band imaging and auto fluorescence imaging.

<Fourth Embodiment>

Next, an endoscope system 1D according to a fourth embodiment will be described. Since the endoscope system 1D of the present embodiment is similar to the endoscope system 1 or the like of the first embodiment, the same components will be assigned the same reference numerals and descriptions thereof will be omitted.

The endoscope system 1D of the present embodiment can perform narrow band imaging and infrared imaging (IRI) as special light imaging in addition to normal light imaging.

Figure 10A:
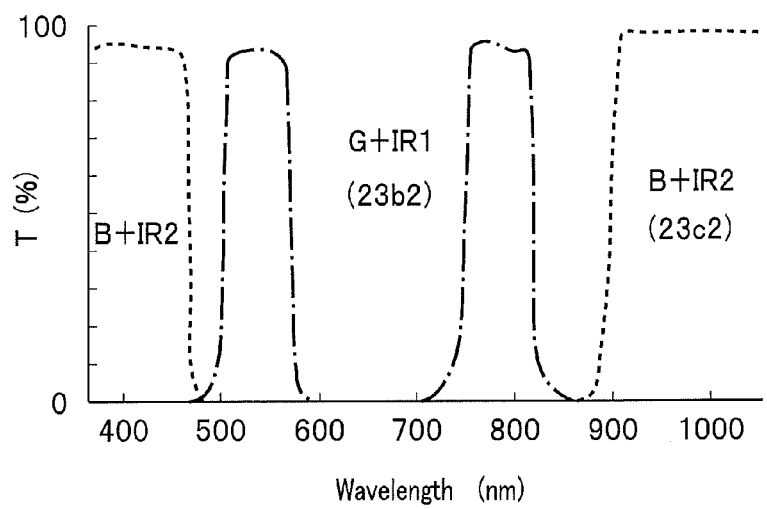
FIG. 10A is a graph illustrating transmission characteristics of filters.
Figure 10B:
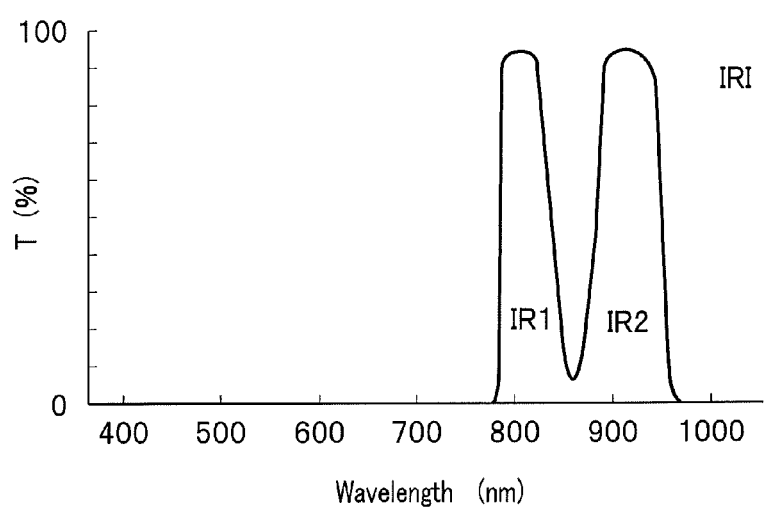
FIG. 10B is a graph illustrating transmission characteristics of filters.
Figure 10C:
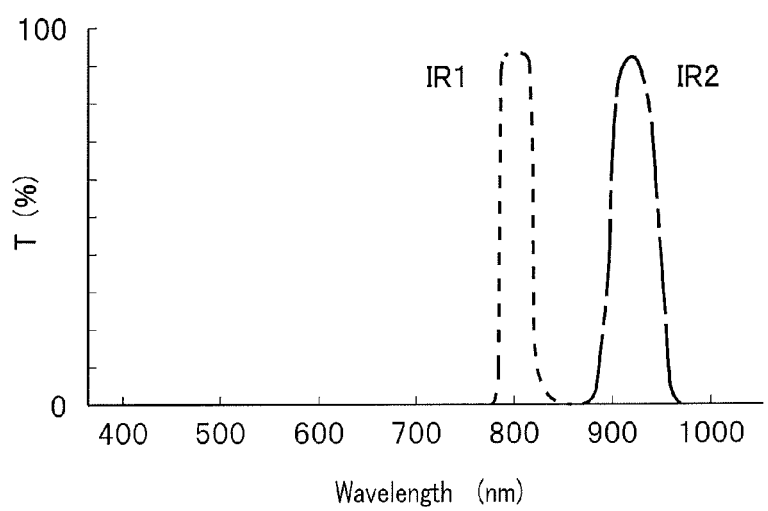
FIG. 10C is a graph illustrating transmission characteristics of filters.

A light source apparatus 20D of the endoscope system 1D includes a band limiting filter 22d which is an IRI filter in the band selection filter section 22. As shown in FIG. 10B, the transmittance of the IRI filter is 93% or above only in an IR1 wavelength band of 800 to 830 nm and an IR2 wavelength band of 910 to 950 nm. Furthermore, the transmittance of a green (G+IR1) filter 23b2 of the first rotational filter section 23D is 90% or above in 780 to 805 nm which is an IR1 wavelength band in addition to the green wavelength band. Furthermore, the transmittance of a blue (B+IR2) filter 23a2 is 90% or above in 920 to 950 nm which is an IR2 wavelength band in addition to the blue wavelength band.

Figure 11A:
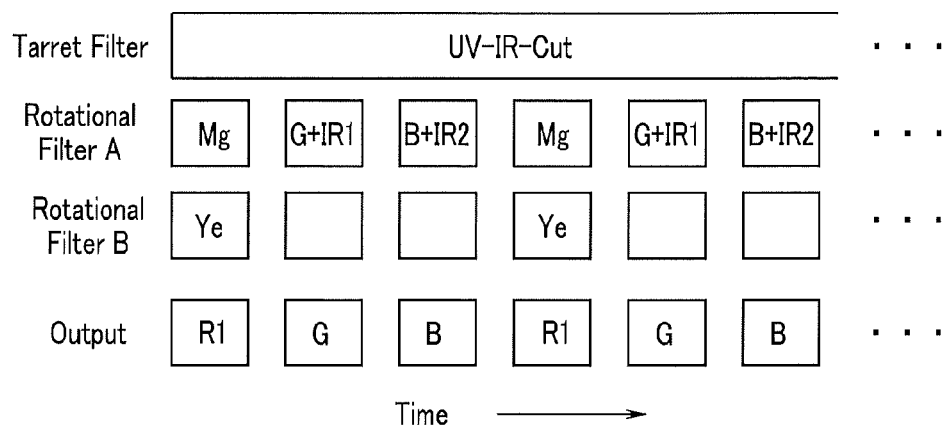
FIG. 11A is a diagram illustrating irradiating light in an endoscope system according to a fourth embodiment.
Figure 11B:
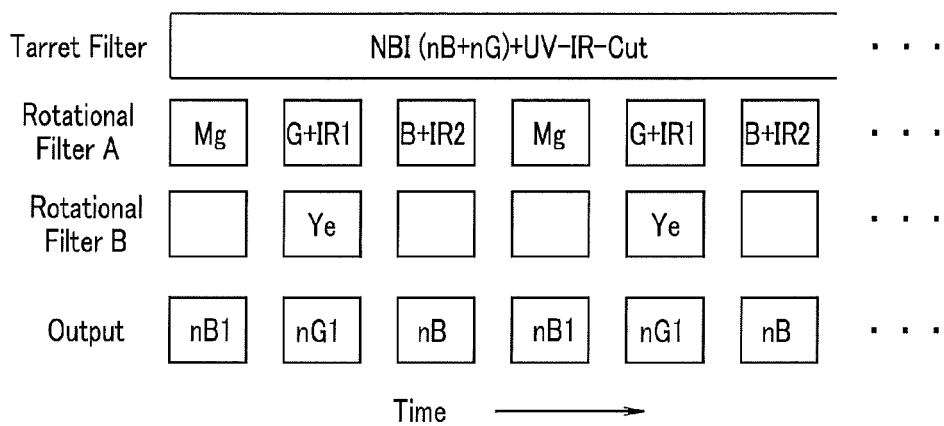
FIG. 11B is a diagram illustrating irradiating light in the endoscope system according to the fourth embodiment.

Operations of the light source apparatus 20D of the endoscope system 1D in the normal light imaging mode and narrow band imaging mode are the same as those of the already described endoscope system 1 or the like as shown in FIG. 11A and FIG. 11B.

Figure 11C:
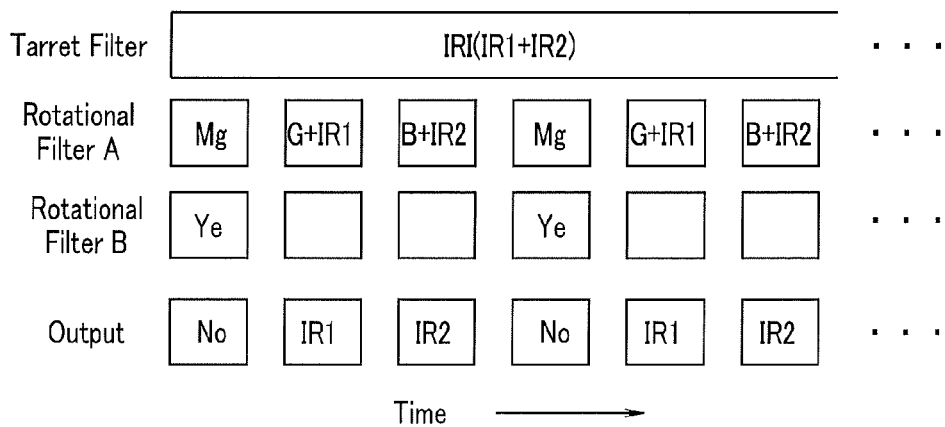
FIG. 11C is a diagram illustrating irradiating light in the endoscope system according to the fourth embodiment.

In the infrared imaging mode, the IRI filter of the band selection filter section 22 is placed in the light path LP. As shown in FIG. 11C, irradiating light in the IR1 wavelength band is supplied when the green (G+IR1) filter 23b2 is placed in the light path LP in the first rotational filter section 23 and irradiating light of the IR2 wavelength band is supplied when the blue (G+IR2) filter 23b2 is placed in the light path LP.

Figure 12A:
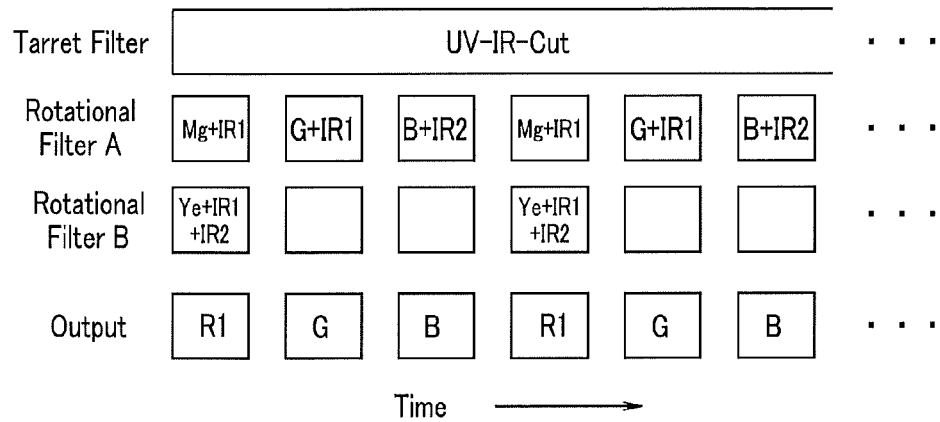
FIG. 12A is a diagram illustrating irradiating light in an endoscope system according to a modification example of the fourth embodiment.
Figure 12B:
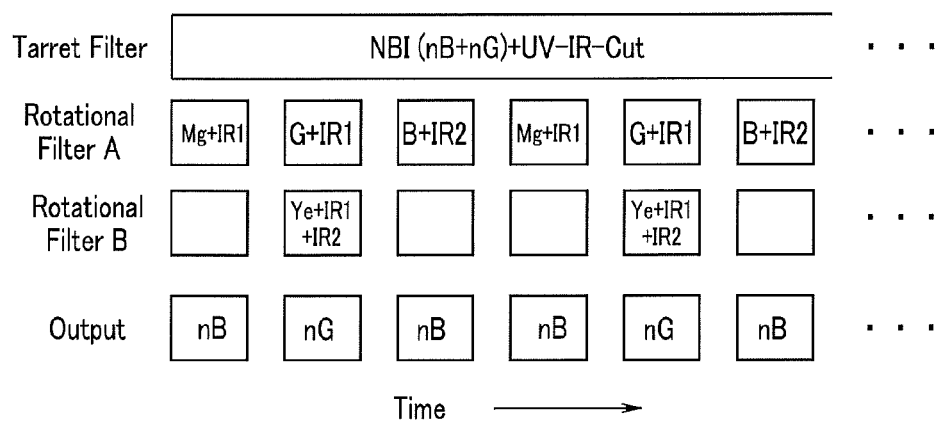
FIG. 12B is a diagram illustrating irradiating light in an endoscope system according to a modification example of the fourth embodiment.
Figure 12C:
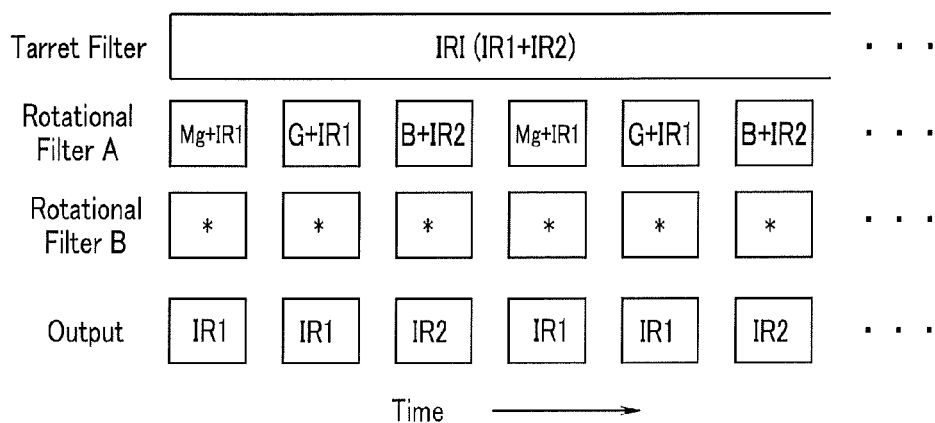
FIG. 12C is a diagram illustrating irradiating light in an endoscope system according to a modification example of the fourth embodiment.

As shown in FIG. 11C, infrared light is not radiated when the Mg filter 23c is placed in the light path LP in the first rotational filter section 23, but as shown in FIG. 12, infrared light in the IR1 wavelength band can be radiated by using the Mg2 (Mg+IR1) filter having a transmission region also in the infrared light region.

The IR1 wavelength band in the above description is equivalent to the IR2 wavelength band and the G filter and Mg filter may have a transmission region in the IR2 wavelength band or the B filter may have a transmission region in the IR1 wavelength band. Furthermore, the G filter and the B filter may have a transmission region in the IR1 wavelength band or the Mg filter may have a transmission region in the IR2 wavelength band.

The endoscope system 1D has the effects of the endoscope system 1 or the like and can further perform narrow band imaging and infrared imaging.

<Supplementary Descriptions>

Although a case has been described above where a magenta filter and a yellow filter are used as complementary color filters, a cyan filter (Cy) may also be used according to the target image (irradiating light) or the combination of the primary color filter and the complementary color filter may also be changed according to the target image (irradiating light) as appropriate.

For example, the Cy filter and the Mg filter that transmit blue light and green light may be combined to supply blue light. In this case, the falling wavelength of transmittance of the Cy filter and the rising wavelength of the Mg filter are preferably 30 nm or above.

Furthermore, the Cy filter and the Ye filter may be combined to supply green light. In this case, the transmittance on the longer wavelength side of the visible light region of the Cy filter and the transmittance of the shorter wavelength side of the visible light region of the Ye filter are preferably 1% or below.

The light source apparatus and the endoscope system of the present invention are not limited to the above-described special light imaging, but are also applicable to other special light imaging. For example, the present invention may also be applicable to an endoscope provided with a light source apparatus for infrared auto fluorescence imaging or photo-dynamic imaging. Here, the infrared auto fluorescence imaging is an imaging method using a fluorescent image in an infrared band. The photo-dynamic imaging is a method of imaging fluorescence by accumulating a photosensitive substance such as porphyrin derivative in a lesion to be treated and furthermore, a photosensitive substance may be caused to produce active oxygen when transitioning from an excited state to a ground state, interfere with cell respiration and thereby denature and necrose cells.

The filter characteristics or the like used in the above descriptions are examples of the specification and the filter characteristics are not limited thereto. For example, for the rotational filter section 23C of the endoscope system 1C of the third embodiment, the Mg filter may not necessarily be placed on the inner and outer circumferences, but may be placed on one of the two. Furthermore, for example, an endoscope system (light source apparatus) capable of performing normal light imaging, narrow band imaging, infrared imaging and auto fluorescence imaging may be configured by combining the components of the endoscope system 1C (light source apparatus 20C) and the components of the endoscope system 1D (light source apparatus 20D).

The present invention is not limited to the aforementioned embodiments, but various changes and modifications can be made without departing from the spirit and scope of the present invention.

What is claimed is:

1. A light source apparatus that can supply illuminating light for normal light imaging and special light imaging, comprising:
    a light source section that generates wideband light;
    a first rotational filter section that can place a first filter that passes light of a first wavelength band, a second filter that passes light of a second wavelength band having a longer wavelength than the first wavelength band or a third filter that passes light of a third wavelength band having a longer wavelength than the second wavelength band and light of the first wavelength band in a light path of the wideband light generated by the light source section;
    a second rotational filter section that can place a fourth filter that passes light of the second wavelength band and light of the third wavelength band in the light path; and
    a band selection filter section that can place a band limiting filter that limits light of the first wavelength band and light of the second wavelength band to a narrow band and intercepts light of the third wavelength band in the light path,
    wherein in a case of the normal light imaging, the first rotational filter section and the second rotational filter section are controllable so that the fourth filter is placed in the light path when the third filter is placed in the light path, and
    in a case of the special light imaging, the band limiting filter is placed in the light path and the first rotational filter section and the second rotational filter section are controllable so that the fourth filter is placed in the light path when the second filter is placed in the light path.

2. The light source apparatus according to claim 1, wherein the first filter and the second filter are primary color filters and the third filter and the fourth filter are complementary color filters.

3. The light source apparatus according to claim 2, wherein the first filter is a blue filter that passes light of a blue wavelength band, the second filter is a green filter that passes light of a green wavelength band, the third filter is a magenta filter that passes light of a red wavelength band and light of a blue wavelength band and the fourth filter is a yellow filter that passes light of a green wavelength band and light of a red wavelength band.

4. The light source apparatus according to claim 3, wherein the wideband light includes infrared light,
    the band selection filter section can place an infrared imaging filter that limits the infrared light to light of a fourth wavelength band and light of a fifth wavelength band in the light path,
    the first filter passes light of the fourth wavelength band and the second filter passes light of the fifth wavelength band, and
    the infrared imaging filter is placed in the light path to thereby allow illuminating light for infrared imaging to be supplied.

5. The light source apparatus according to claim 4, wherein in the infrared imaging, the first and second rotational filter sections are controllable so that the fourth filter is placed in the light path when the third filter is placed in the light path.

6. The light source apparatus according to claim 4, wherein the second filter passes light of the fourth wavelength band or light of the fifth wavelength band.

7. The light source apparatus according to claim 1, wherein the special light imaging is at least one of narrow band imaging and auto fluorescence imaging.

8. The light source apparatus according to claim 1, wherein illuminating light for illuminating a digestive tract of a subject is supplied.

9. An endoscope system that can perform normal light imaging and special light imaging, comprising:
   an insertion portion that comprises an image pickup section at a distal end portion and a light guide inserted therein;
   a light source apparatus that supplies illuminating light via the light guide; and
   an image processing unit that processes an image picked up by the image pickup section; and
   a control section,
   wherein the light source apparatus comprises:
   a first rotational filter section that can place a first filter that passes light of a first wavelength band, a second filter that passes light of a second wavelength band having a longer wavelength than the first wavelength band or a third filter that passes light of a third wavelength band having a longer wavelength than the second wavelength band and light of the first wavelength band in a light path of the wideband light generated by the light source section; and
   a second rotational filter section that can place a fourth filter that passes light of the second wavelength band and light of the third wavelength band in the light path; and
   a band selection filter section that can place a band limiting filter that limits light of the first wavelength band and light of the second wavelength band to a narrow band and intercepts light of the third wavelength band in the light path, and
   the control section controls, in a case of the normal light imaging, the first rotational filter section and the second rotational filter section so that the fourth filter is placed in the light path when the third filter is placed in the light path, and
   places, in a case of the special light imaging, the band limiting filter in the light path and controls the first rotational filter section and the second rotational filter section so that the fourth filter is placed in the light path when the second filter is placed in the light path.

10. The endoscope system according to claim 9, wherein the first filter and the second filter are primary color filters and the third filter and the fourth filter are complementary color filters.

11. The endoscope system according to claim 10, wherein the special light imaging is narrow band imaging the first filter is a blue filter that passes light of a blue wavelength band, the second filter is a green filter that passes light of a green wavelength band, the third filter is a magenta filter that passes light of a red wavelength band and a blue wavelength band and the fourth filter is a yellow filter that passes light of a green wavelength band and a red wavelength band.

12. The endoscope system according to claim 11, wherein in the special light imaging when brightness of an image obtained by the illuminating light via the first filter is a predetermined value or below, the image processing unit performs addition processing on the image obtained by the illuminating light via the first filter and the image obtained by the illuminating light via the third filter.

* * * * *